United States Patent [19]

Naka

[11] Patent Number: 5,474,677

[45] Date of Patent: Dec. 12, 1995

[54] AUTOMATIC MEASUREMENT METHOD OF GLYCOHEMOGLOBIN AND SAMPLE INJECTION VALVE

[75] Inventor: Michio Naka, Kyoto, Japan

[73] Assignee: Kabushiki Kaisha Kyoto Daiichi Kagaku, Kyoto, Japan

[21] Appl. No.: 340,795

[22] Filed: Nov. 15, 1994

Related U.S. Application Data

[63] Continuation of Ser. No. 80,395, Jun. 21, 1993, abandoned, which is a continuation of Ser. No. 751,625, Aug. 23, 1991, abandoned, which is a continuation of Ser. No. 218,742, Jul. 13, 1988, abandoned.

[30] Foreign Application Priority Data

Jul. 14, 1987 [JP] Japan .................................... 62-175713

[51] Int. Cl.$^6$ .......................... B01D 15/08; B01D 15/00; G01N 33/72; G01N 30/04
[52] U.S. Cl. .......................... 210/656; 210/198.2; 422/70; 436/67; 436/161
[58] Field of Search .................................... 422/70; 436/47, 436/48, 52, 53, 67, 161; 210/181, 198.2, 635, 656; 530/417

[56] References Cited

U.S. PATENT DOCUMENTS

| | | |
|---|---|---|
| 4,098,592 | 7/1978 | Prescott et al. .................. 210/198.2 |
| 4,399,227 | 8/1983 | Niederau et al. .................. 436/67 |
| 4,409,335 | 10/1983 | Hanamoto et al. .................. 436/67 |
| 4,438,204 | 3/1984 | Deeg et al. .................. 436/67 |
| 4,465,774 | 8/1984 | Huang et al. .................. 436/67 |
| 4,649,122 | 3/1987 | Lee .................. 436/67 |
| 4,806,468 | 2/1989 | Wagner et al. .................. 436/67 |
| 4,861,728 | 8/1989 | Wagner .................. 436/67 |
| 4,876,188 | 10/1989 | Smith et al. .................. 436/67 |
| 4,879,039 | 11/1989 | Takahashi et al. .................. 436/67 |
| 4,966,695 | 10/1990 | Joshua .................. 210/198.2 |
| 5,292,663 | 3/1994 | Yamazaki et al. .................. 436/67 |
| 5,294,336 | 3/1994 | Mizuno et al. .................. 210/198.2 |

OTHER PUBLICATIONS

Snyder, L. R. et al., "Introduction to Modern Liquid Chromatography", Wiley & Sons, Inc., New York (1979) pp. 113–117; 551–552.

*Primary Examiner*—John Kim
*Attorney, Agent, or Firm*—Darby & Darby

[57] ABSTRACT

A number of blood samples collected in sample vessels are allowed to stand by as whole blood or blood cell layer, the sample vessels are sent into sampling part in order, the blood sample suctioned from the sampling nozzle is diluted by mixing with hemolyzing liquid containing labile $HbA_{1c}$ removing reagent, a part of the mixture is led to a sample-loop of sample injection valve and injected into the column of high pressure liquid chromatograph at a specified time after mixing start, hemoglobin fractions are measured in the state of removal or lowering of labile $HbA_{1c}$, and the rate of stable glycohemoglobin is determined from thus obtained chromatogram.

1 Claim, 3 Drawing Sheets

AUTOMATIC MEASUREMENT METHOD OF GLYCOHEMOGLOBIN AND SAMPLE INJECTION VALVE

This is a continuation, of application Ser. No. 08/080, 395, filed Jun. 21, 1993, now abandoned, which is a continuation of application Ser. No. 07/751,625, filed Aug. 23, 1991, abandoned, which is a continuation of Ser. No. 07/218,742, filed Jul. 13, 1988 abandoned.

BACKGROUND OF THE INVENTION

The present invention relates to an improved automatic measurement method of glycohemoglobin based on the principle of high pressure liquid chromatography and to an improved sample injection valve used for a high pressure liquid chromatograph.

Glycohemoglobin ($HbA_1$) attaching glucose to hemoglobin is often found in diabetes patients, and particularly $HbA_{1c}$ has been an important measurement item as an index for a health screening such as a medical checkup or for a long-term control of diabetes. Because, $HbA_{1c}$ exists most abundantly in glycohemoglobin ($HbA_1$) and the increase by diabetes is much more than in the other component, and moreover the value of $HbA_{1c}$ shows a significant correlation with an average blood sugar level in hunger for past 1~3 months.

Glycohemoglobin includes $HbA_{1a}$ and $HbA_{1b}$ besides $HbA_{1c}$, and these fractions are measured by colorimetry, electrophoresis, minicolumn method, or high pressure liquid chromatography. Among them, in the area of clinical tests, recently high pressure liquid chromatography (HPLC) has been prevalent in view of required time and separation.

A so-called stable type in $HbA_{1c}$ shows a significant correlation with a past blood sugar level and besides a labile type does not so. The rate of the latter is said to be 10~15% in all $HbA_{1c}$ in hunger on healthy human. In this labile $HbA_{1c}$, the N end of β-chain of hemoglobin and the reductive end of glucose form a reversible Shiff-base combination, which generates and degrades in a relatively short time depending on blood sugar levels. Therefore, it exists in diabetes patients more than in healthy, sometimes being 10~20% to all $HbA_{1c}$. After meal it exists more than in hunger, being effected largely by the condition in collecting blood.

Stable $HbA_{1c}$ is generated from labile $HbA_{1c}$ gradually, continually, and irreversibly, reflecting the past long-term blood sugar levels. Thus, the separate measurement of the stable type only is desirable. However, both of the stable and labile types closely resemble structurally, being considerably difficult to separate by liquid chromatography.

As a method against this, the elevation of separation has been conducted by using a long high-separation column. Though this method has a merit that the denaturalization of glycohemoglobin by chemical treatment may not occur, the analyzing time of ten and several min or more is necessary to gain a good separation, insufficiently dealing with the increase of samples or urgent measurement. Moreover, this type of column is long leading to the apparatus of large type and high cost.

As another method for separately measuring the stable $HbA_{1c}$, there is a method wherein the labile $HbA_{1c}$ is removed by degrading chemically in pretreatment. This is based on that the temporary combination (Shiff base) of labile $HbA_{1c}$ and glucose is easy to degrade. For instance, washed red cells are incubated in isotonic phosphoric acid buffer solution (37° C., 4 hrs) or in physiological saline solution (room temperature, 14 hrs) to release glucose from labile $HbA_{1c}$.

Or, there is also a method wherein whole blood added a hemolyzing reagent is incubated at 35° C. for ten and several hrs. It reduces the level of labile $HbA_{1c}$ by hemolyzing and diluting a sample, particularly having a large effect in the acidic area below pH 6, a fast reaction speed, and a large effect at an elevated temperature. Further, the addition of the reagent for removing labile $HbA_{1c}$ containing boric acid on the market which has been used for minicolumn method enlarges the effect.

However, the pretreatment requires time, and together with the degradation of labile $HbA_{1c}$, the degradation and change of other glycohemoglobin and pure hemoglobin ($HbA_o$) proceed also at the same time.

The hemolyzing type has had a defect that the quantity of stable $HbA_{1c}$ varies with the time elapsed after hemolyzing and the temperature experienced till measurement. Particularly, in the case of the automatic measurement of a number of samples, there has been a disadvantage that the dilution of blood sample by the hemolyzing liquid containing a degrading reagent changes the sample measured later in samples on standby by excessive proceeding of reaction because of longer time elapsed.

SUMMARY OF THE INVENTION

The object of the present invention is to provide a method for measuring stable $HbA_{1c}$ with good reproducibility and high accuracy with preventing the degradation and change of glycohemoglobin other than labile $HbA_{1c}$ together with the analysis of glycohemoglobin using the labile $HbA_{1c}$ removing reagent (degradation reagent) by high pressure liquid chromatography. In addition, the object of the invention is to provide a method for analyzing glycohemoglobin wherein the structure of the apparatus is relatively simple and the treatment and preparation of sample are easy.

Further, the object of the invention is to provide a optimum sample injection valve to control the temperature of mixing solution of sample (not limited to blood sample) and reagent in a high pressure liquid chromatograph.

DETAILED DESCRIPTION OF THE INVENTION

Figure 1:
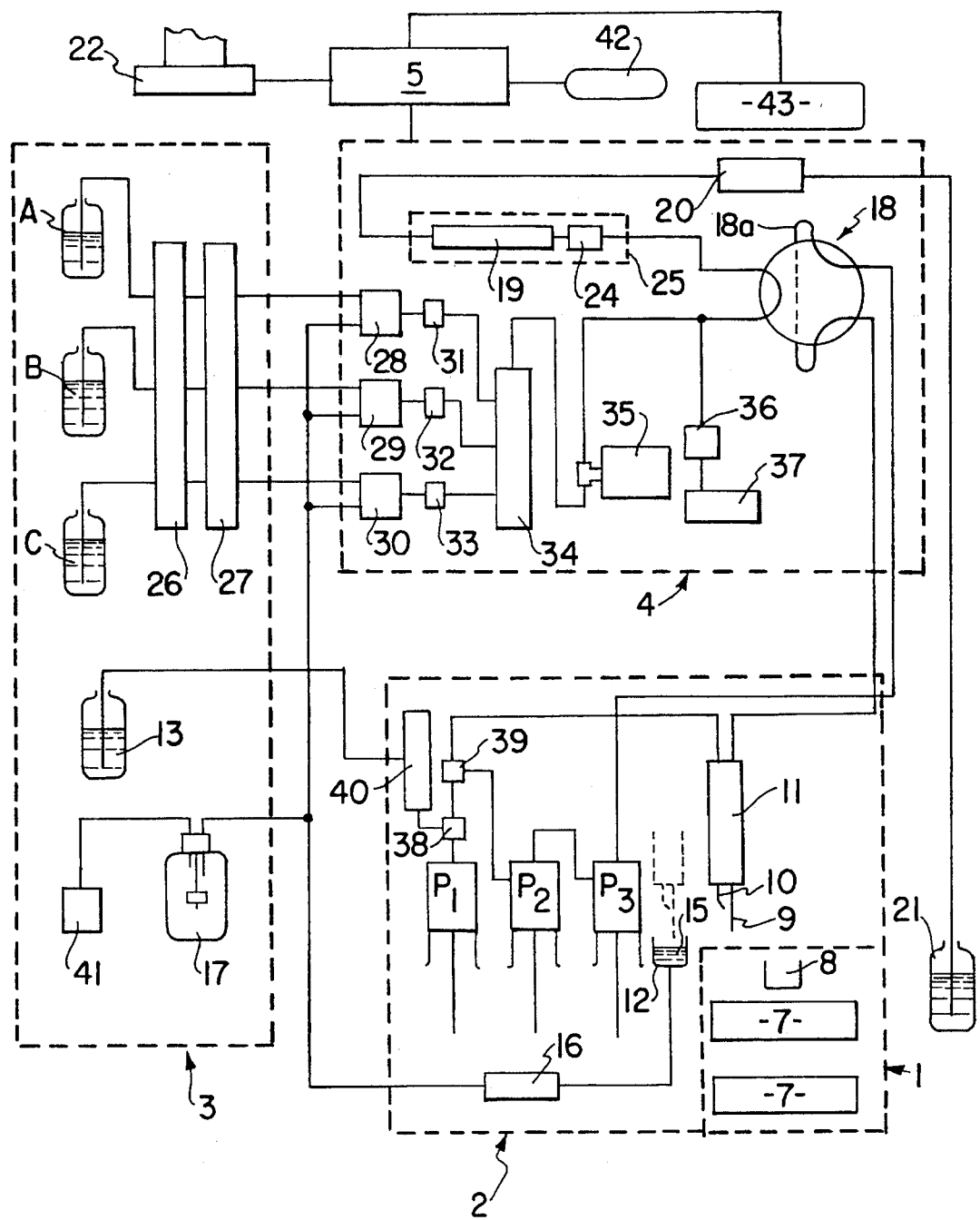
FIG. 1 is a flow diagram showing an example of glycohemoglobin automatic measurement apparatus embodied the invention method.

The object mentioned above is attained by allowing a number of blood samples as whole blood or blood cell layer to stand by, sampling a sample at the time of its measurement order, mixing the sample by quickly diluting with hemolyzing liquid containing a labile $HbA_{1c}$ removing reagent, and by injecting the mixing liquid into a high pressure liquid chromatograph column at a specified time after mixing start. Hereafter, "sample" refers to whole blood sample (or blood cell layer), and "specimen" refers to mixing liquid diluted the sample by hemolyzing liquid.

Further, the reaction is accelerated by warming till the mixing liquid (specimen) is injected into column, enabling the speedier measurement. When this warming is made at the loop part of sample injection valve, preparation of other warming zone or useless warming of specimen is unnecessary, enabling space and energy saving.

Further, the invention saves time of mixing reagent manually, and prevents errors by manual mixing and the change of sample till measurement after mixing.

The procedure of the invention and the structure of the measurement apparatus will be described in the following.

First, blood samples collected from each patient or subject are put into sample vessels such as blood tubes or sampling cups, and allowed to stand by at the sample holding part as whole blood or blood cell layer. Since whole blood or blood cell layer centrifuged whole blood is used, pretreatment is unnecessary and simple. Blood cell layer may be uased by making use of remaining plasma after the other tests, but whole blood also deposits blood cell components at the bottom after standing for long time. Accordingly, sampling is preferably made from the vicinity of the bottom. Though there is a variation in the rate of red cells in blood sample, the rate of $HbA_{1c}$ to $HbA_o$ or the other $HbA_1$ is constant in each sample, being no problem. An anticoagulant is usually added to blood sample. As anticoagulants, ones on the market such as heparin or EDTA-2Na may be used.

Each sample vessel is held in a holding device such as rack, snake-chain, or turn-table in a large number, and sent into the sampling position in order.

At the sampling part, a specified quantity 1 to few μl of sample is suctioned from a sampling nozzle by the suction action of pump, and diluted by hemolyzing liquid containing a labile $HbA_{1c}$ removing reagent separately supplied, and mixed. The dilution is tens–hundreds-fold, preferably 10–400-fold.

As the procedure of sampling and dilution, various structures and changes are considered depending on the structures and combinations of various types of pumps. In short, preferable is the structure wherein blood samples sampled within few tens sec–few min just before measurement are diluted with hemolyzing-washing liquid and injected into column through sample injection valve at a specified time after mixing start. It is necessary that these actions are made automatically and continuously and a means is devised to prevent contamination.

As labile $HbA_{1c}$ removing reagents, boric acid, phosphoric compunds, or reagents on the market containing them are used. Ones having acidic pH are preferable. As hemolyzing agents, general ones on the market are used.

As a column, one for high pressure liquid chromatography such as filled with spherical ion-exchange gel (anion, cation) is used, and the treatment time of specimen is confined by the separation.

The state of reaction proceeding after hemolyzing depends upon the property of the labile $HbA_{1c}$ removing reagent, and is associated with the time and temperature after reaction start. The time for measurement is the sum of the operation time for sampling, diluting, mixing, feeding, and washing and the warming time. The short measurement time is preferable to treat a number of samples. If the ability of degrading labile $HbA_{1c}$ of the reagent is low, the shortening of the reaction time is made by warming the specimen (mixed liquid) pass in the temperature range without trouble such as the change of sample. In this case, the temperature of whole or part of the pass including the sample injection valve part is so controlled that the time till measurement is constant in view of the analyzing time and the degradation ability of the reagent. In view of the degradation ability and the warming time, the warming temperature is 30°–65° C., preferably 40°–55° C. The temperature above 65° C. causes the change of protein undesirably. That below 30° C. may require cooling in summer.

In the following, the washing liquid will be described. The washing liquid washes the sampling nozzle and each pass to prevent contamination after measuring the late specimen. The structure of the invention, wherein the sample is mixed after dilution by hemolyzing liquid, requires naturally 2 feeding systems of washing and hemolyzing liquid. As a matter of course, this structure may be used, but combining the both as the hemolyzing-washing liquid lessens one of the feeding pumps, simplifying the piping and feeding sequence.

In the invention, the mixing liquid (specimen) is injected into column at a specified time after the mixing start of blood sample and hemolyzing liquid. In case of the mistimed mixing start in calculating back from the next injection timing for some reason such as smoothless shift of rack or mistimed wedging measurement, blank measurement action is preferably made without mixing and injection in this time. This mistimed mixing has no problem in the case of the use of only one type of eluting solution, but in the case of 2 types or more of eluting solution of different concentration or pH, the mistimed injection loses the balance in the column.

EXAMPLE

The present invention method will be described in detail by showing the following example of the measuring apparatus of glycohemoglobin embodied the invention method. In the example, hemolyzing liquid which also serves as washing liquid is used and a specimen is warmed in the sample-loop at the sample injection valve.

Figure 2:
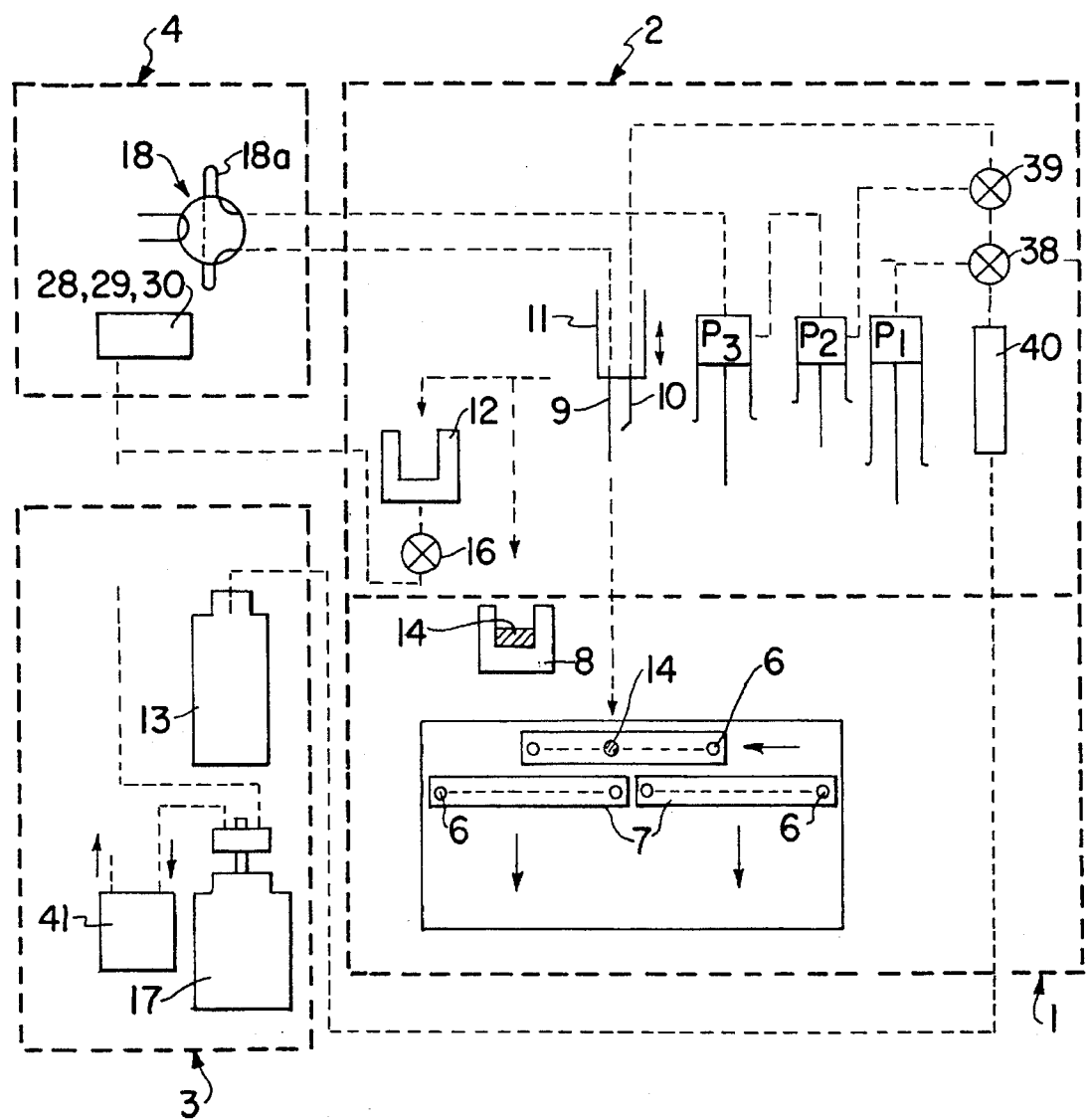
FIG. 2 is a flow diagram showing the sampling part.
Figure 3:
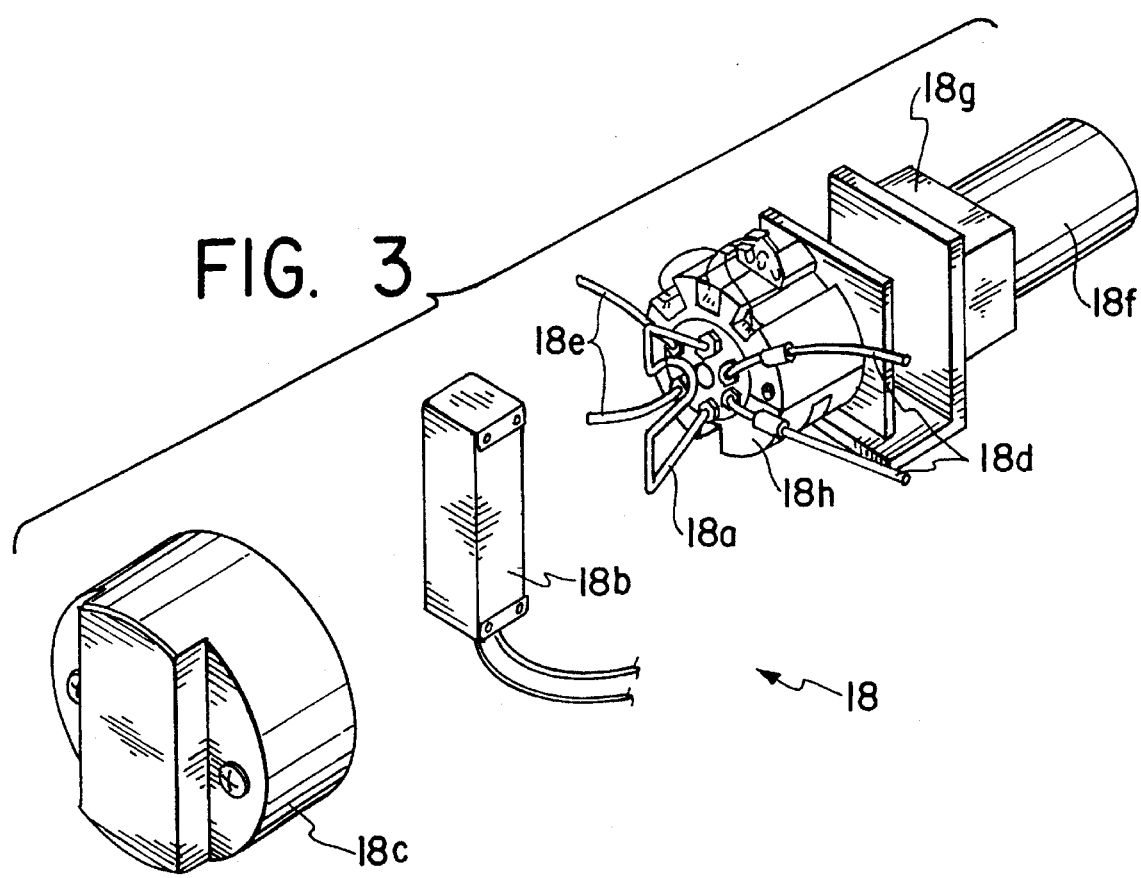
FIG. 3 is a rough oblique showing the sample injection valve.

FIG. 1 is a flow-diagram showing an example of glycohemoglobin automatic measuring apparatus embodied the invention method. FIG. 2 is a flow-diagram showing the sampling part. FIG. 3 is a rough oblique showing the sample injection valve.

The apparatus is composed of a sample holding part(1) for holding and pooling plural sample vessels containing whole blood sample or blood cell layer, a sampling part(2) for sampling and diluting-mixing with hemolyzing liquid, a bottle-unit part(3) for receiving vessels for eluting solution, hemolyzing-washing liquid, and waste solution, an analyzing part(4) including a sample injection valve, column, and photometric means, a memory-control part for controlling the whole apparatus function, memorizing and calculating measurement values, and outputting the results on indication apparatus such as printer together with patient number and measuring date, and a keyboard for inputting working command. As the memory-control part, a microcomputer(5) is, for instance, used. For the indication apparatus, a digital indicator may be used besides.

The structure and function of each part will be described in the following. In the sample holding part(1), a number of racks(7) holding plural sample vessels(6) are set. Each rack(7) is so driven towards the arrow direction that the sample vessel(6) is placed at the sampling position in order. A wedged measuring port(8) for urgent measurement may be prepared.

The sampling part(2) has a sampling nozzle mechanism(11) with two nozzles(9, 10), a hemolyzing-washing liquid pump($P_1$), a sample suction pump($P_2$), a specimen injection pump($P_3$), and a dilution pouring vessel(12). The capacity of the sample suction pump($P_2$) is 1–few μl, and that of the washing liquid pump($P_1$) and the specimen injection pump($P_3$) is hundreds µl. The sampling nozzle mechanism(11) moves up and down with rotation. The hemolyzing-washing liquid(13) is prepared by dissolving the above-mentioned labile $HbA_{1c}$ degrading reagent and hemolyzing agent in the dilution liquid of sample. In the example, this liquid is also used for washing pumps, nozzles, and other flow-lines. In the invention, a sample(14) refers to a whole blood sample or blood cell layer, and a specimen(15) refers to a solution prepared by diluting the sample(14) with the washing liquid(13) to tens-hundreds-fold.

At the sampling part(2), first a specified quantity of sample(14) is suctioned from the first nozzle(9) by driving the sample suction pump($P_2$). Next, the sampling nozzle mechanism(11) is moved to over the dilution pouring vessel(12), and the washing liquid(13) is discharged from the second nozzle(10) to wash the outside of the first nozzle(9). For this object, the second nozzle(10) has the tip bent towards the first nozzle(9). The waste liquid is led to a drain bottle(17) at the bottle-unit part(3) through a waste liquid valve(16). Next, the sample(14) and a specified quantity of hemolyzing-washing liquid(13) are discharged into the dilution pouring vessel(12) by driving the pumps($P_1$, $P_2$). The both(13, 14) are stirred by this discharge. Further, the both may be sufficiently stirred and mixed by repeating suction and discharge by the first nozzle(9). Thus mixed specimen(15) is suctioned from the first nozzle(9) by suctioning action of the specimen injection pump($P_3$) and fed into the sample injection valve(18) at the analyzing part(4). (the state in FIG. 1 and FIG. 2) Next, the dilution pouring vessel(12), piping, and the first nozzle(9) outside are washed by the hemolyzing-washing liquid(13), and the waste liquid is discarded and preparations for the next sample suction are made.

On the other hand, the specimen(15) fed into the sample-loop(18a) at the sample injection valve(18) is warmed by being held in the warmed sample-loop(18a). The sample-loop(18a) is, as showed in FIG. 3, surrounded by a loop warmer(18b), and further the loop warmer(18b) and the main part of the sample injection valve(18) are covered by a temperature keeping cover(18c). In the figure, symbol(18d) is pipe for specimen, (18e) pipe for eluting solution, (18f) motor,(18g) geer box, and (18h) block for keeping temperature. The temperature keeping cover(18c) is screwed to the block(18h).

In warming by this method, there is no useless energy and no injection of unwarmed specimen part into column(19) because of sure warming of specimen only in the sample-loop(18a).

Figure 4:
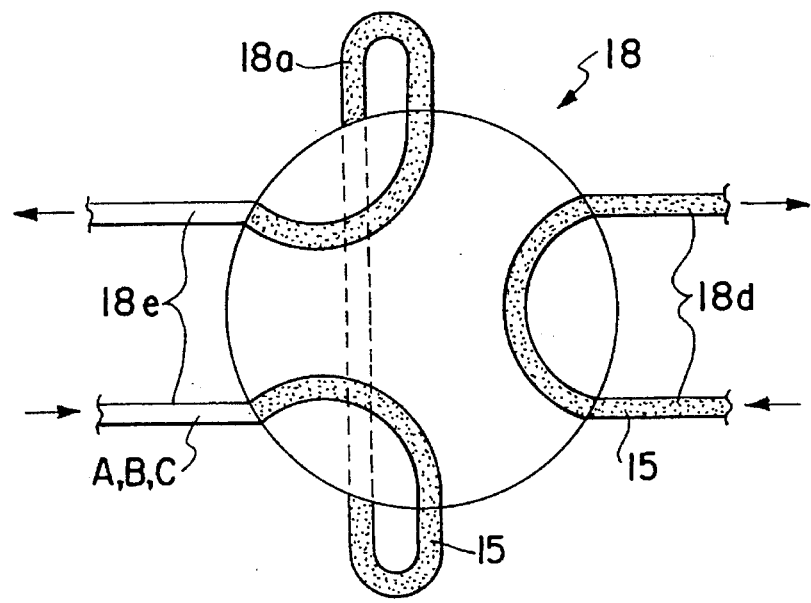
FIG. 4 is a plan showing the state of the sample injection valve when injecting sample into column.

Next, the motor(18f) of sample injection valve(18) is rotated to the state showed as FIG. 4 and the specimen(15) in the sample-loop(18a) is injected into column(19) by being pushed out by the eluting solution sent from the bottle-unit part(3). Each component of specimen(15), $HbA_{1a}$, $HbA_{1b}$, $HbA_{1c}$, and $HbA_o$, is separated in column(19), and subjected to photometry by photometer(20) in order and discarded in drain vessel(21). The photometric results are sent to microcomputer(5) and each fraction pattern, elution time of peak, and content % of each component are calculated to be printed out at printer(22). When filter(24) is set before column(19) to remove impurities and the whole is kept in a thermostat(25), stable measurements are performed.

Table-1 shows the summary of operations mentioned above based on FIG. 2 concerning the action of pumps($P_1$, $P_2$, and $P_3$) and the flow state of flow-exchange valve(38, 39) for the hemolyzing-washing liquid(13). In each pump, ↓ shows suction ↑ discharge, and blank stop.

TABLE 1

| pump. valve step | P1 | P2 | P3 | 38 | 39 | operation |
| --- | --- | --- | --- | --- | --- | --- |
| 1 | ↓ | ↓ | | ⊖ | ⊕ | sample is suctioned, hemolyzing-washing liquid is suctioned |
| 2 | ↑ | | | ⊕ | ⊕ | hemolyzing-washing liquid is discharged to wash nozzle-outside |
| 3 | ↓ | | | ⊖ | ⊕ | hemolyzing-washing liquid is suctioned |
| 4 | ↑ | ↑ | | ⊕ | ⊕ | blood sample and hemolyzing-washing liquid are discharged to mix |
| 5 | | | ↓ | ⊕ | ⊕ | specimen is suctioned and the part is fed to sample-loop to be warmed |
| 6 | | | ↑ | ⊕ | ⊕ | specimen is injected into coloumn by exchanging sample injection valve and remaining specimen is discharged |
| 7 | ↓ | | | ⊖ | ⊕ | hemolyzing-washing liquid is suctioned |
| 8 | ↑ | | | ⊕ | ⊖ | sample-loop and other flow lines are washed |

In operation mentioned above, hemolyzing-washing liquid(13) of 450 µl for dilution of 1.5 µl of sample(14) is 300-fold in dilution. The optimum conditions of the warming time and temperature of specimen(15) are 2 min 40 sec. at 48° C., though depending on the degradation ability of a labile $HbA_{1c}$ removing reagent, under the above-mentioned dilution in the case of the use of hemolyzing liquid containing a labile $HbA_{1c}$ removing reagent of phosphoric acid compound which is on sale with the name of "21H" by the present applicants. The degradation of labile $HbA_{1c}$ is almost completely made with 2 min at 60° C., 3 min. at 40° C., and 4 min at 33° C.

In the example, 3 types of eluting solution are used. Each eluting solution, (A), (B), and (C), based on the flow sequence, is sent to a manifold(34) in order by each exchange valve(31, 32 and 33) through heating coil(26), cooling coil(27), and debubbler (28, 29, and 30). Each eluting solution which entered one flow line at manifold(34) is sent to sample injection valve(18) by feed pump(35), injected into column(19), and flows into drain vessel(21) through photometer(20) with carrying specimen(15). In the figure, symbol(36) is a pressure detector, and(37) a damper.

In FIG. 1 and FIG. 2, symbol (38, 39) is a exchange valve for hemolyzing-washing liquid(13), (40) a out of liquid sensor for hemolyzing-washing liquid(13), (41) a suction air pump for drain bottle(17), (42) a indicator, and (43) a operation keyboard.

The above-mentioned description is for the case of measuring samples continuously arranged, in which case the working in a constant sequence results in a constant time from dilution to injection. However, in case sample vessels are placed on rack(7) uncontinuously because of variation in the time in collecting blood, an excessive irregular time is required to find the next sample. Also in case a sample vessel is set on a wedging port for urgent measurement, the mistimed suction of blood sample may occur. Thus, in finishing injection of specimen(15) into column(19) the next sample is found and, by calculating back from the next injection time, dilution is preferably started timely.

On dilution start, when the missing of the next injection already became clear, the continous operation of one sequence without the mixing and injection of specimen into column enables the stable measurement to continue without harming the column balancing condition even if in the case of the use of 3 types of eluting solution of different concentration or pH.

COMPARISON WITH THE CONVENTION METHOD

Comparison with the Blood Cell Washing Method by Isotonic Phosphoric Acid Buffer Solution The blood cell washing method by isotonic phosphoric acid buffer solution, which has been practiced as a standard method for removing labile $HbA_{1c}$ (pretreatment), was compared with the method of the present invention. Table-2 shows the results.

As the results, the method of the invention produced the similar effects with the conventional method in removal of labile $HbA_{1c}$ fraction. Further, compared to the combination of the blood cell washing method and 21H, the

TABLE 2

| faction condition | Measurement value (%) | | | |
|---|---|---|---|---|
| | $A_1 a + A_1 b$ | F | $L\text{-}A_1 c + S\text{-}A_1 c$ | $A_1$ |
| 21L | 1.5 | 0.2 | 5.9 | 7.4 |
| 21H | 1.4 | 0.2 | 5.2 | 6.6 |
| "S" + 21L | 1.4 | 0.2 | 5.2 | 6.6 |
| "S" + 21H | 1.4 | 0.2 | 5.2 | 6.6 |

F: Glycohemoglobin HbF
L-$A_1$ c: Labile $HbA_1$ c
S-$A_1$ c: Stable $HbA_1$ c
"S": Blood cell washing method by isotonic phosphoric acid buffer solution more lowering of labile $HbA_{1c}$ fraction and the increase of $A_{1a+b}$ by change were not observed.

In the case of no pretreatment and no use of labile $HbA_{1c}$ removing reagent(21L), all values are high. The difference between 21L and other treatments in L-$A_{1c}$+S-$A_{1c}$ is assumed to be labile $HbA_{1c}$. In the example, labile $HbA_{1c}$ is ca 0.7% of whole hemoglobin. Measurements were practiced under the following conditions.

21: Hemolyzing-Washing Liquid Without Labile $HbA_{1c}$ Removing Reagent
nonionic surface-action agent 1 g/l
potassium di-hydrogen phosphate 0.1 g/l
potassium mono-hydrogen phosphate 0.3 g/l
pH 7.5
21H: Hemolyzing-Washing Liquid Containing Labile $HbA_{1c}$ Removing Reagent
nonionic surface-active agent 1 g/l
phosphoric acid compound 0.1 g/l
KOH 0.3 g/l
pH 6
"S"+21L: Conventional Blood Cell Washing Method is Used Washed blood cells are added to isotonic phosphoric acid buffer solution, and labile $HbA_{1c}$ is removed by incubation for 6 hrs at 37° C. with continuous rotary mixing.

Then, the blood cell layer is collected and diluted with 21L to 300-fold to measure.

"S"+21H:21H was Combined to Blood Cell Washing Method

Similarly, with "S"+21L, the blood cell layer treated with isotonic phosphoric acid buffer solution is collected and diluted with 21H to 300-fold to measure.

Subject: healthy normal human, test just after collecting blood. Measurement conditions: according to the example method, warming temperature 48° C., warming time 2 min 40 sec, measurement time 4 min, and n=5.

As mentioned above in detail, the present invention relates to the improved method of automatic measurement of glycohemoglobin based on the principle of high pressure liquid chromatography which comprises allowing a number of blood samples collected from each patient as whole blood or blood cell layer to stand by at a sample holding part, sampling just before measurement (before tens sec~few min), mixing with dilution by hemolyzing-washing liquid containing labile $HbA_{1c}$ removing reagent, and injecting into column of high pressure liquid chromatograph at a specified time after mixing start. As necessary, warming may be made from dilution to injection into column.

Therefore, the invention has the following many excellent effects. ① Compared to conventional method wherein a long column of high quality is used, more rapid measurement can be practiced and the same degree of accuracy can be obtained. ② Labor of mixing reagent manually is saved, enabling accurate measurement without error due to manual dilution. ③ Pretreatment is unnecessary because of the use of whole blood or blood cell layer centrifuged it. ④ Since the sample is not diluted by hemolyzing reagent in advance, the change of sample is not occur till measurement and stable $HbA_{1c}$ can accurately be measured by preventing the degradation or change of glycohemoglobin other than labile $HbA_{1c}$. ⑤ Since the measurement value is not effected by labile $HbA_{1c}$, there is no restriction by time of blood-collecting and it is not a burden on patients. ⑥ Further, since a sample is hemolyzed just before measurement and injected into column always at constant timing, stable measurements can be made. Particularly, since the balancing condition is not harmed even if samples are set uncontinuously, the chromatogram's patterns are stable.

The sample injection valve warms the sample liquid and reagent at specified temperature for specified time. Since only specimen is warmed surely, there is no useless energy and no risk of injection of unwarmed part into column, leading to accurate control. The valve of the invention can be prepared by improving a conventional sample injection valve simply. Since the other warming device is not required, there is a merit of space-saving.

I claim:

1. An automatic HPLC method for measuring glycohemoglobin which uses two or more types of eluting solution comprising the steps of:

mixing a blood sample with a hemolyzing liquid containing a labile $HbA_{1c}$ degrading agent to form a mixture, providing an HPLC sample injection valve unit comprising:

a sample injection valve body having a plurality of channels, one of said channels having an input for receiving an HPLC sample, a sample loop which connects two channels of said valve body and extends externally of the valve body, a heating element in close proximity to said externally extending sample loop to heat the loop and the sample therein, and means for regulating the temperature of said heating element, directing a portion of said mixture into the sample loop of the HPLC sample injection valve unit at a specified time after mixing, heating said portion of said mixture in said sample loop under control of said temperature regulating means to a temperature between about 30° C. to about 65° C. to promote a labile $HbA_{1c}$ degrading reaction of said portion, pushing out said heated portion contained in said sample loop into an HPLC column by a first one of said two or more types of eluting solutions at a predetermined time after the mixing step to allow for degradation of the labile $HbA_{1c}$, measuring the glycohemoglobin separated in the HPLC column, sending a second one of the two or more eluting solutions into the HPLC column at a predetermined time after pushing out the heated portion in the sample loop into the HPLC column, repeating said sending step for any of the remaining two or more eluting solutions, and conducting the sending step without sending the sample into the HPLC column and without performing the measuring step in order to maintain the heating time of the sample in the sample loop and maintain one of the column thermal and pH conditions if the directing step is mistimed and is not performed substantially at said specified time after mixing.

* * * * *